US008752261B2

(12) United States Patent
Van Sciver

(10) Patent No.: US 8,752,261 B2
(45) Date of Patent: Jun. 17, 2014

(54) MOUNTING STENTS ON STENT DELIVERY SYSTEMS

(75) Inventor: Jason Van Sciver, Los Gatos, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 592 days.

(21) Appl. No.: 12/831,878

(22) Filed: Jul. 7, 2010

(65) Prior Publication Data
US 2012/0010693 A1    Jan. 12, 2012

(51) Int. Cl.
B21D 39/04    (2006.01)
(52) U.S. Cl.
USPC ................................. 29/282; 29/272; 72/402
(58) Field of Classification Search
USPC ........... 29/255, 508, 447, 516, 270, 271, 272, 29/280, 282, 283, 235, 283.5; 623/1.11; 72/402; 606/108, 139, 140, 194
See application file for complete search history.

(56) References Cited

U.S. PATENT DOCUMENTS

| | | | |
|---|---|---|---|
| 5,836,965 A | 11/1998 | Jendersee et al. | |
| 5,913,871 A | 6/1999 | Werneth et al. | |
| 5,976,181 A | 11/1999 | Whelan et al. | |
| 6,018,857 A * | 2/2000 | Duffy et al. | 29/407.01 |
| 6,629,350 B2 | 10/2003 | Motsenbocker | |
| 6,745,445 B2 | 6/2004 | Spilka | |
| 6,863,683 B2 | 3/2005 | Schwager et al. | |
| 6,931,899 B2 * | 8/2005 | Goff et al. | 72/18.1 |
| 7,010,850 B2 | 3/2006 | Hijlkema et al. | |
| 7,316,148 B2 | 1/2008 | Asmus et al. | |
| 7,761,968 B2 * | 7/2010 | Huang et al. | 29/447 |
| 7,762,804 B1 * | 7/2010 | Stupecky | 425/392 |
| 7,886,419 B2 * | 2/2011 | Huang et al. | 29/407.08 |
| 7,945,409 B2 * | 5/2011 | Furst et al. | 702/81 |
| 8,123,793 B2 | 2/2012 | Roach et al. | |
| 8,225,474 B2 * | 7/2012 | Arcand et al. | 29/272 |
| 2002/0143382 A1 | 10/2002 | Hijlkema et al. | |
| 2004/0078953 A1 | 4/2004 | Spilka | |
| 2004/0096538 A1 | 5/2004 | Goff et al. | |
| 2004/0106973 A1 | 6/2004 | Johnson | |
| 2005/0119720 A1 | 6/2005 | Gale et al. | |
| 2005/0143752 A1 | 6/2005 | Schwager et al. | |
| 2005/0159802 A1 | 7/2005 | Furst et al. | |
| 2006/0047336 A1 | 3/2006 | Gale et al. | |

(Continued)

FOREIGN PATENT DOCUMENTS

| | | |
|---|---|---|
| EP | 1 295 570 | 3/2003 |
| WO | WO 99/55406 | 11/1999 |
| WO | WO 01/35861 | 5/2001 |

OTHER PUBLICATIONS

U.S. Appl. No. 11/326,797, filed Jan. 6, 2006, Abbate et al.

(Continued)

Primary Examiner — Lee D Wilson
Assistant Examiner — Joel Crandall
(74) Attorney, Agent, or Firm — Squire Sanders (US) LLP

(57) ABSTRACT

A system for mounting a stent on a balloon catheter includes two positioning and alignment stations, which are used to prepare a stent and catheter for crimping using the same crimping head. The system is configured for automated assembly of the stent and catheter prior to crimping. A catheter and stent are placed on a computer-controlled carriage that delivers the stent and catheter to the crimper head. Before placing the stent and catheter into the crimper head, an automated alignment system locates the stent between balloon markers.

21 Claims, 9 Drawing Sheets

(56) References Cited

U.S. PATENT DOCUMENTS

| | | |
|---|---|---|
| 2006/0196073 A1 | 9/2006 | Parker |
| 2007/0006441 A1 | 1/2007 | McNiven et al. |
| 2007/0271763 A1 | 11/2007 | Huang et al. |
| 2007/0282433 A1 | 12/2007 | Limon et al. |
| 2007/0289117 A1 | 12/2007 | Huang et al. |
| 2008/0016668 A1 | 1/2008 | Huang et al. |
| 2008/0033523 A1 | 2/2008 | Gale et al. |
| 2008/0033524 A1 | 2/2008 | Gale |
| 2008/0033526 A1* | 2/2008 | Atladottir et al. ............ 623/1.11 |
| 2008/0147164 A1 | 6/2008 | Gale et al. |
| 2008/0275537 A1 | 11/2008 | Limon |
| 2009/0001633 A1 | 1/2009 | Limon et al. |
| 2009/0088829 A1 | 4/2009 | Wang et al. |
| 2009/0299452 A1* | 12/2009 | Eidenschink et al. ....... 623/1.11 |
| 2010/0004735 A1 | 1/2010 | Yang et al. |
| 2010/0025894 A1 | 2/2010 | Kleiner et al. |
| 2011/0307046 A1* | 12/2011 | Bourang et al. ............. 623/1.11 |

OTHER PUBLICATIONS

U.S. Appl. No. 11/330,927, filed Jan. 11, 2006, Wu et al.

International Search Report and the Written Opinion for PCT/US2008/077108 mailed Feb. 2, 2009, 6 pgs.

International Search Report and the Written Opinion for PCT/US2011/043234 mailed Nov. 3, 2011, 13 pgs.

* cited by examiner

MOUNTING STENTS ON STENT DELIVERY SYSTEMS

BACKGROUND OF THE INVENTION

1. Field of the Invention

The present invention relates to drug-eluting medical devices; more particularly, this invention relates to systems, apparatus and methods for mounting to a delivery balloon a balloon-expandable stent, such as a polymeric stent.

2. Background of the Invention

FIGS. 1A and 1B depict perspective views of a prior art crimping station used to crimp a balloon expandable stent to a deployment balloon of a balloon catheter. The crimping station includes a crimper head 220, an interactive screen 216 for programming a crimping sequence, e.g., diameter reduction, dwell times between successive crimps, temperature control of the crimper jaws, etc. A carriage 242 aligns a catheter 209 with the opening 222 to the crimper head 220 and advances the distal end 209b of the catheter, where a stent 100 and the balloon are located, into the crimper head 220. The crimper head 220 includes three rollers 223, 224 and 225, which place a clean sheet of non-stick polymer material between the crimper jaws and stent 100 to avoid buildup of coating material on the jaws when plural stents having drug-polymer coatings are being crimped to balloon catheters.

FIG. 1B shows a perspective view of the carriage 242, which includes a slidable block 250 holding catheter 209. The block 250 is used to advance the catheter distal end 209b and stent 100 into and out of the crimper head 220 using knob 274. The catheter 209 is held within a groove 252 formed on the block 250. The catheter 209 shaft is retained in the groove 252 by a pair of cylindrical rods 253, 254 which are rotated down to trap the catheter shaft in the groove 252 before it is advanced into the crimper head 220 via the opening 222. The rods 253, 254 are rotated from the closed position (as shown) to an open position to allow the catheter 209 to be removed from the groove 252 by rotating hinge arms 253a, 254a clockwise (as indicated by A, B). A handle 255 is connected to the hinge arms 253a, 254a and rotated in direction C to move the hinge arms 253a, 254a to the open position. A rail 273 is connected to the block 250 at block extension 250a. The block 250 is displaceable over a distance "S". An operator manually moves the distal end 209b and stent 100 towards or away from the crimper head 220 using the knob 274. The rail 273 is received within, and slides over a passage of a support 272, which is mounted to the table of the crimper station. The block 250 is received within, and slides along grooves (not shown) of a support piece 260. An abutment 275 of the support piece 260 serves as a stop to indicate when the catheter distal end 209b is positioned properly within the crimper head 220.

In operation, the operator manually places the catheter 209 within the groove 252 and holds it in place by rotating the handle clockwise to position the rods 253, 254 into the position shown in FIG. 1B. The operator then manually places the stent 100 over the balloon. Prior to inserting the distal end 209b within the crimper head 220, the operator must ensure that the stent is properly positioned on the balloon, i.e., the operator must ensure that the stent is located between marker bands of the balloon before placing the stent within the crimper head 220, so that when the balloon is inflated, the stent will expand properly within a patient's vasculature. the stent and balloon are then advanced into the crimper head by push the carriage forward until block 250 strikes or abuts the stop 275. When the block 250 hits the stop 275 the stent and balloon are in the desired position within the crimper head.

Preparing a stent-catheter assembly utilizing equipment such as that described above, and/or production techniques whereby operators dedicated to manually loading a stent on a balloon and ensuring the assembly is positioned/aligned properly so that the stent is properly crimped to the crimping head, is burdensome. In the case of high volume polymer stent-catheter assembly production there can be significantly more time spent properly crimping a polymer stent compared to a metal stent. Moreover, existing procedures for placing and aligning a stent, just prior to crimping has become more problematic and time-consuming as the lengths of deployment balloons have been shortened to about the length of a stent. Since the balloon length is matched more closely to the length of the stent (for purposes of avoiding damage to vascular tissue when the stent is deployed within a body) there is less margin for error by the operator. Given the small sizes for stents and balloons, great care must therefore be exercised by the operator to ensure that the stent is properly located on the balloon before crimping. If the stent is not properly positioned on the balloon before crimping, both the stent and catheter must the discarded.

The art recognizes a variety of factors that affect a polymeric stent's ability to retain its structural integrity when subjected to external loadings, such as crimping and balloon expansion forces. These interactions are complex and the mechanisms of action not fully understand. According to the art, characteristics differentiating a polymeric, bio-absorbable stent of the type expanded to a deployed state by plastic deformation from a similarly functioning metal stent are many and significant. These and related challenges faced in the manufacture and crimping of polymer stents to balloons are discussed in U.S. application Ser. Nos. 12/776,317 and 12/772,116.

One aspect of polymer stents, as compared to metal stents, that has presented certain challenges is the procedures required to ensure an acceptable yield when crimping large numbers of polymer stents to balloon catheters, as explained in more detail in applications U.S. application Ser. Nos. 12/776,317 and 12/772,116, as well as improving efficiency in crimping large numbers of polymer stents to balloons so that production-level polymer stent crimping does not impose unacceptable delays in the manufacturing process. The operation of crimping devices are time consuming when being used to crimp polymer stents and current production yields are less than favorable.

In view of the foregoing, there is a need to improve upon existing crimping processes, such as in the case of crimping polymer stents to balloon catheters.

SUMMARY OF THE INVENTION

The invention provides an apparatus, system and process for crimping a stent to a balloon catheter. According to one aspect of the disclosure, a stent mounting system includes a crimper head and a pair of stations, located on opposite sides of the crimper head, for positioning first and second stent and catheter assemblies and aligning the first and second stents on their respective balloon catheters prior to crimping the stents to the balloons. The crimper head is adapted for receiving the stent and catheter assemblies from both stations to perform a crimping process at the same time. The system incorporates computer-controlled processes for reducing much of the labor typically required by an operator, e.g., a technician, when preparing a stent and catheter for crimping and monitoring the crimping process. Automated, computer-controlled processes replacing manual pre-crimping processes can increase yield, since there is less likelihood that a stent and catheter will be improperly located within the crimper head, which can result in uneven crimping over the length of a stent, or a stent not properly aligned with a balloon markers prior to crimping. By using automated, computer-controlled process the time required for crimping can be reduced, and production yields increased. Moreover, more operator time is made available, so that multiple crimping sequences can be monitored by the same operator.

These and other advantages of the invention are particularly worth noting when polymer stents are crimped. In contrast to a metal stent, a polymer stent must be crimped at a much slower rate due to the inherent limitations of the material compared at that of a metal. This slower process can produce significant bottlenecks during stent-catheter production. By automating manual crimping tasks, the overall time needed to crimp a polymer stent can be noticeably reduced. Polymer stents are more sensitive to fracture when crimping produces irregular bending or twisting of struts, since a polymer material suitable for a load-bearing stent, e.g., PLLA, is far more brittle than a metal. Inaccurate crimping within the crimper head, e.g., non-uniform applied forces through the crimper jaws when the stent and catheter are not properly located, or positioned within the crimper head, is therefore more likely to cause fracture in polymer stent struts. Accuracy and repeatability in the crimping process is therefore more critical to increased yield for a polymer stent than a metal stent. According to one aspect of the invention, there is a discovered need for more automation in a crimping process for polymer stents, whereas there is less need for automation when crimping metal stents. A crimping sequence for a polymer stent can be about five times longer than a metal stent. This 5-fold increase in crimping time, when multiplied out by the number of polymer stent-balloon assemblies crimped during a production run, poses unique challenges in planning and resource allocation, which is contrast to the time and resource allocation needed for crimping metal stents. A primary reason for the delay is the need to crimp the polymer material more slowly to reduce instances of crack creation or propagation, and to reduce recoil when the crimping jaws are removed from the stent surface.

Existing systems for crimping a stent to a balloon require an operator to both manually align stents between balloon markers, properly insert the stent and balloon assembly within a crimper head and then verify that the stent is being properly crimped in mid-process. The invention substantially overcomes many of the drawbacks of requiring an operator to perform these tasks by introducing automated processes for positioning and aligning a stent and catheter for crimping.

According to the disclosure, the system may be configured to automate the following manual tasks:

Manually positioning a catheter distal end at the entrance of the aperture and then manually advancing the stent and catheter within the crimper head. According to one aspect of the invention, a computer automatically advances the stent and catheter into the crimper head after an operator has verified, e.g., by a laser light identifying the proper location of the catheter's proximal balloon seal relative to a reference point, that the catheter has been properly placed within a carriage that advances the catheter and stent into the crimper head under computer control. A laser positioning system or a camera may be used to locate the proper placement of the catheter relative to the carriage, as well as to signal to a processor controlling the carriage motion forward into the crimper head that the stent-catheter as been positioned properly within the crimper head, once this signal is received, an actuator advances the stent-catheter assembly into the crimper head. The device illustrated in FIGS. 1A-1B, by contrast, utilizes a mechanical stop 275 to indicate to the operator that the stent-catheter assembly is located properly within the crimper head. However, it has been discovered that this manner of positioning the stent-catheter assembly within the crimper head can cause the stent to displace relative to the balloon, thereby throwing the stent out of alignment. The invention recognizes that a mechanical stop, even when found suitable for positioning a metal stent within a crimper head, introduces problems for polymer stents, particularly when the polymer stent has a much larger diameter than the balloon. As a solution to this problem, a servo mechanism is used to advance the stent-catheter assembly into the crimper head at a rate which reduces the chance that the stent will move relative to the balloon.

Manually aligning the stent between balloon markers. According to one aspect of the invention, an imaging system is used to image the stent and catheter and then determine, e.g., by pattern recognition software, whether the stent is properly aligned. If the stent is not properly aligned, the stent position relative to balloon markers is adjusted using computer-controlled actuators. The actuators may be controlled by servo mechanisms driven by a processor, which processor may utilize a camera or laser alignment system and may incorporate controller logic with or without a feedback loop during the adjustment.

Manual inspection of the stent on the balloon after an initial, or pre-crimp, to ensure that the stent has not shifted relative to the balloon markers within the crimper. If the stent has shifted, then the operator manually adjusts the stent before placing the stent and catheter back into the crimper. According to another aspect of the invention, the crimping process is under computer control after the stent-catheter assembly is loaded onto a carriage and the operator activates the process. The stent-catheter assembly is placed in the crimper head, a pre-crimp is performed, then the stent-catheter are withdrawn from the crimper head. The imaging system is then activated to verify that the stent is aligned with the balloon markers. After verifying that the stent is between the balloon markers, the stent-catheter assembly is advanced again into the crimper head to perform the final crimp. No operator involvement is necessary.

Performing the above manual processes, one after another, for a first stent, then a second stent after the first stent has been crimped to a balloon. According to another aspect of the invention, a crimper head is provided for simultaneously crimping first and second stent and catheter assemblies in one crimping sequence. Hence, the automated positioning, aligning, and verification after pre-crimp steps described above can be performed concurrently for two stent and catheter assemblies.

The invention addresses the need to improve alignment processes for stent-catheter assemblies that demand tighter alignment tolerances. Short balloon tapers and shorter marker bands drive more precise stent positioning. Precise position correction of the stent is difficult to perform manually by an operator and requires special training. Manually positioning can result in stent, coating and/or balloon damage if not done correctly. This positioning task is made more difficult when the stent is manufactured to have a deployed or over-deployed diameter (a large starting diameter is chosen to provide improved mechanical characteristics when the stent is expanded to its deployed diameter). The relatively large annular gap between the stent and folded balloon presents significant positioning challenges.

Consistent with these objectives and in view of the foregoing problems and/or needs in the art addressed/met by the invention, the invention provides, in one aspect, a crimper head, a first station and a second station disposed adjacent the crimper head and configured to receive, respectively, a first stent and a first balloon catheter assembly and a second stent and a second balloon catheter assembly, the first station and the second station each include an aligning portion and a positioning portion, and a processor for simultaneously crimping both the first stent to the first balloon catheter and the second stent to the second balloon catheter using the crimper head. When a user command, e.g., start crimping sequence, is received by the processor, the processor, e.g., a local computer, causes (a) the first station to align the first stent with the first balloon catheter and the second station to align the second stent with the second balloon catheter using the respective first and second station aligning portions, (b) the first station to insert the first stent and first balloon catheter into the crimper head and the second station to insert the second stent and second balloon catheter into the crimper head using the respective first and second station positioning portions, and (c) the crimper head to perform a crimping sequence for crimping both the first stent to the first balloon catheter and the second stent to the second balloon catheter.

According to another aspect of the invention, there is provided machine executable code residing on a machine readable storage medium for performing tasks (a), (b) and (c). The machine readable code may include code for operating the aligning portion using a control system (with or without a feedback loop).

The aligning portion may include a camera for obtaining an image of a stent on a balloon, machine readable instructions accessible to the processor for analyzing the image to determine whether the stent is misaligned on the balloon, an actuator for displacing one of the stent and balloon relative to the other of the stent and balloon if a misalignment of the stent relative to the balloon was detected from the analyzed image, and a controller for controlling movement of the actuator for displacing one of the stent and balloon relative to the other using the actuator according to an offset of the stent relative to the balloon.

According to another aspect of the invention, there is a method for crimping a stent to a balloon of a balloon catheter, the balloon having balloon markers identifying a proper alignment of the stent with the balloon, the method including preparing the balloon catheter for crimping including placing the catheter on a movable carriage; verifying that the stent is aligned with the balloon including collecting at least one image of the stent and balloon and then analyzing the image to verify that the stent is between the balloon markers; after the verifying step, inserting the stent and balloon into a crimper; and crimping the stent to the balloon.

According to another aspect of the invention, there is a crimping method for a polymer stent including a final crimp followed by a dwelling period. During the dwell period the balloon and stent are maintained at an elevated temperature and a leak test for the balloon is performed while the stent-catheter assembly is being gripped by the crimper jaws.

According to another aspect of the invention, there is an apparatus for crimping a polymer stent to a balloon catheter, comprising: a crimper head having jaws; an aligning portion; a positioning portion; a processor in communication with the crimper head, aligning portion and the positioning portion; and machine executable code, executable by the processor, for performing a crimping process.

The machine executable code includes a first code for aligning the polymer stent with the balloon of the balloon catheter and positioning the polymer stent and balloon within the crimper head, and a second code for crimping the polymer stent to the balloon, including setting the crimper jaws at a final crimping diameter followed by a dwell time to allow stress relaxation to occur within the polymer stent and to perform a balloon test including inflating the balloon to a pressure and then measuring the pressure over a time period to detect a leak in the balloon.

The scope of the methods and apparatus of the invention also encompass processes that crimp a stent as substantially described in US Pub. No. 2010/0004735 and US Pub. No. 2008/0275537. The thickness of the tube from which the stent is formed may have a thickness of between 0.10 mm and 0.18 mm, and more narrowly at or about 0.152 mm. The stent may be made from PLLA. And the stent may be crimped to a PEBAX balloon.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

DETAILED DESCRIPTION OF EMBODIMENTS

Throughout this disclosure, the balloon expandable implant will be called a "stent", whether the description is referring to an implant made in whole or part of a metal material or a polymeric material such as PLLA. In some instances, the term "scaffold" may be used, which is specifically referring to a biodegradable, polymer implant.

Figure 2:
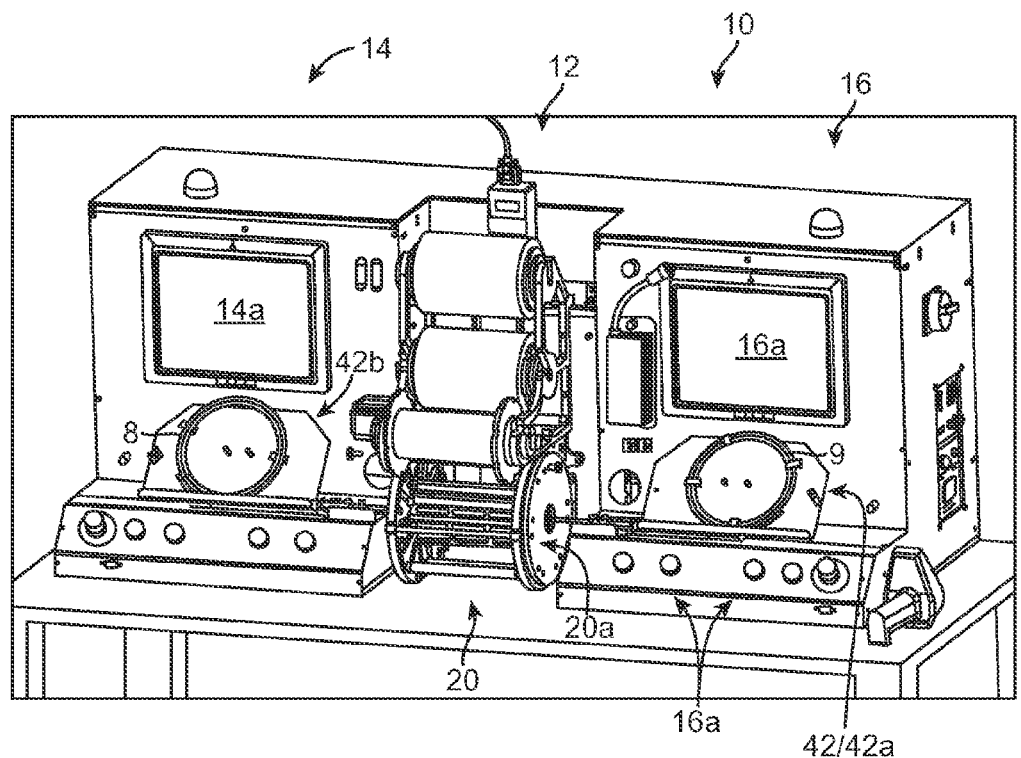
FIG. 2 is a perspective view of a stent mounting system configured for positioning and aligning two pair of stent-catheter assemblies at stations on left and right sides of a crimper head and then crimping the stents to their respective catheters using the crimper head, and using a single crimping cycle. In one aspect of the disclosure, the process is automated, involving little if any operator involvement once the stent-catheter assembly has been placed on carriages at the left and right sides of the crimper head.

FIG. 2 illustrates a stent mounting system 10 according to one aspect of the disclosure. The stent mounting system 10 is configured for positioning a stent on a delivery balloon, then crimping the stent to the balloon in an automated fashion. The system 10 is preferably constructed so that two stents may be simultaneously loaded onto separate balloon catheters, then each placed within a crimper head by a computer-controlled positioning and alignment system. Both stents are then crimped to their respective balloon using the same crimper head. As such, two stents may be simultaneously crimped to catheters during a single crimping sequence. The attending operator need only perform a relatively straight-forward assembly of the stent and catheter, and then mount the stent-catheter assembly on a carriage. A start sequence button is pressed, at which point the remainder of the process is hands-off, thereby alleviating the operator from much of the manual labor that is typically required with existing systems.

Referring again to FIG. 2, system 10 includes left and right positioning and alignment stations 14, 16 located on left and right sides, respectively, of a crimping apparatus 12, which includes the crimping head 20, e.g., an iris-type crimper, and rollers for dispensing a thin sheet of a non-stick polymer material between jaws of the crimping head 20 and a stent to be crimped. Coiled catheters 8, 9 are shown mounted on respective computer-controlled left and right moving carriages 42a, 42b portions of the positioning and alignment stations 14, 16. The carriage portions 42a, 42b may perform various functions associated with an automated stent positioning and alignment process, such as positioning the catheter distal end (where the balloon is located) within the appropriate location in the crimping head 20 and aligning the stent on the balloon of the catheter prior to initiating a crimping sequence. After the stent is properly aligned relative to balloon markers, the catheter with stent is advanced into the crimper head 20 to start the crimping sequence. The stent may then be reduced in diameter to a final crimped state before being withdrawn from the crimper, or partially reduced in diameter, removed to verify proper placement on the balloon, then re-inserted into the crimper to complete the crimping process.

Figure 3:
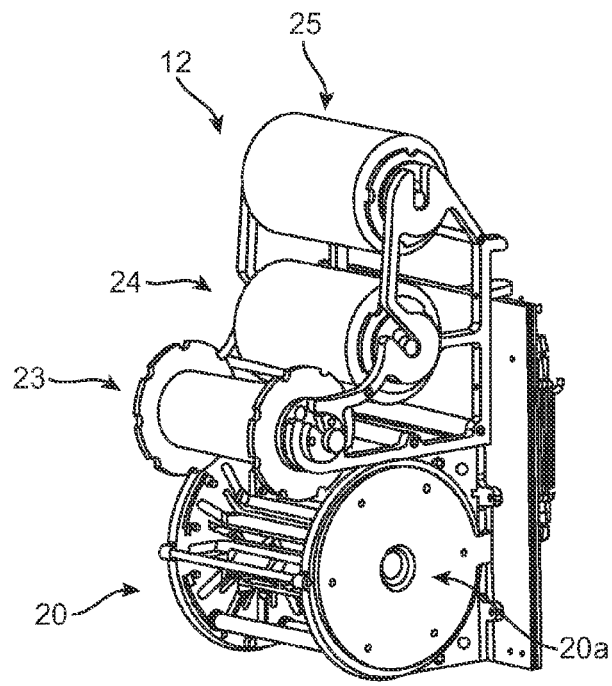
FIG. 3 is a perspective view of a mounting apparatus of the system of FIG. 2 including a crimper head and dispensing rolls.

Referring to FIG. 3, there is shown a perspective view of the mounting apparatus 12. As mentioned above, this portion of the mounting system 10 includes a crimper head 20 and dispensing rolls. The crimper head 20 may be an iris type crimper, an example of which is described in US Pub. No. 2003/0070469. The crimper head 20 includes left and right apertures for passage of the stent and catheter into the crimper head 20 via the left and right positioning and alignment systems 14, 16, respectively (aperture or opening 20a is viewable in the perspective views of FIGS. 2 and 3). Preferably, the crimper head 20 is configured with a compliance offset feature which allows it to properly crimp one or two stents. The compliance offset feature may be implemented by an adjustment of the travel of the crimper jaws on one end when only one stent is being crimped. Without adjustment of jaw loading between two vs. one stents being crimped at the same time, the crimper jaws will produce an uneven force distribution over the length of the stent.

One favorable aspect of a crimper head configured to simultaneously crimp two stents as depicted in FIGS. 2 and 3 is uniformity of the applied load on the stents and bearings of the crimper head. Stent designs can range from 8-80 mm and longer for some applications. Due to catheter fixturing limitations, the proximal edge of the stent is inserted the same distance into the crimp head for all stent sizes. The crimp head can experience high torsional loading in the bearings and diameter disparity between the right hand side and left hand side when a stent of short length is disposed on only one of these sides. By having stents located on both sides of the crimper head the load becomes more evenly distributed, or balanced, thereby providing more uniform resistance during the crimp process.

Three rolls 23, 24, 25 are used to position a clean sheet of non-stick material between the crimping jaws and stent prior to crimping. For example, upper roll 25 holds the sheet secured to a backing sheet. The sheet is drawn from the backing sheet by a rotating mechanism (not shown) within the crimper head 20. The used sheet is gathered by the mid roll 24 after crimping and the backing sheet is collected by the lower roll 23. As an alternative to rollers dispensing a non-stick sheet, each stent may be covered in a thin, compliant protective sheath before crimping.

The dispensed sheet of non-stick material (or protective sheath) is used to avoid buildup of coating material on the crimper jaws for stents coated with a therapeutic agent held within a polymer carrier. The sheet is replaced by a new sheet after each crimping sequence. By advancing a clean sheet after each crimp, accumulation of coating material from previously crimped stents can be avoided. The film is also beneficial when crimping a polymer stent. When metal jaws of a crimper apply pressure to struts of a polymer stent, damage can occur to the struts due to the difference in hardness between the metal and polymer. The polymer film provides a more compliant surface between the jaws and the stent struts to avoid pitting of the stent struts during crimping.

Left positioning and alignment station 14 has the same characteristics as right station 16. Therefore, the remaining discussion applies to either station 14 or 16. Right alignment station 16 includes a display which may be an interactive display 16a for modifying, or simply monitoring a pre-programmed positioning and alignment sequence for a stent and catheter, and subsequent crimping sequence. Information about the process for the particular stent is retrievable from an input stent ID. After scanning in the stent ID via a barcode or receiving the stent ID via an RFID transmitter on the stent holder, the station 16 may upload from a remote storage area process information including parameters/recipes for crimping the particular stent to a catheter, e.g., balloon pressures, dwell times, diameter reductions, temperature, etc. Additional information may be uploaded from the stent ID, such as stent and balloon sizes, which additional information is used to assist with an automated alignment of the stent on the catheter, discussed below.

Control buttons on the front panel 16a of the station 16 may be provided to initiate or abort intermediate phases of a crimping process, e.g., control buttons for initiating/aborting an alignment of the stent on catheter, clamping or releasing the catheter to/from the carriage 42a, aborting a crimping step, advancing the stent and catheter into, or removing the stent and catheter form the crimper head 20, etc.

As indicated above, a polymer sheet is disposed between the stent and crimper jaws. It has been found that a significant static charge can be present on these sheets. Additionally, a static charge can build up when the polymer stent is slid over the balloon surface, or during pre-handling of the stent. For a polymer stent having a much larger diameter than the balloon, these static charges can cause the stent to be thrown out of alignment, either when resting on the balloon or when the stent-catheter assembly is initially introduced to the crimper head and in proximity of the charged polymer sheets. For a polymer stent crimping process, it is desirable to remove or minimize this static charge prior to inserting the stent-catheter assembly into the crimper head. For example, anti-static air may be directed into the crimper head and over the stent-catheter assembly prior to crimping.

Figure 4A:
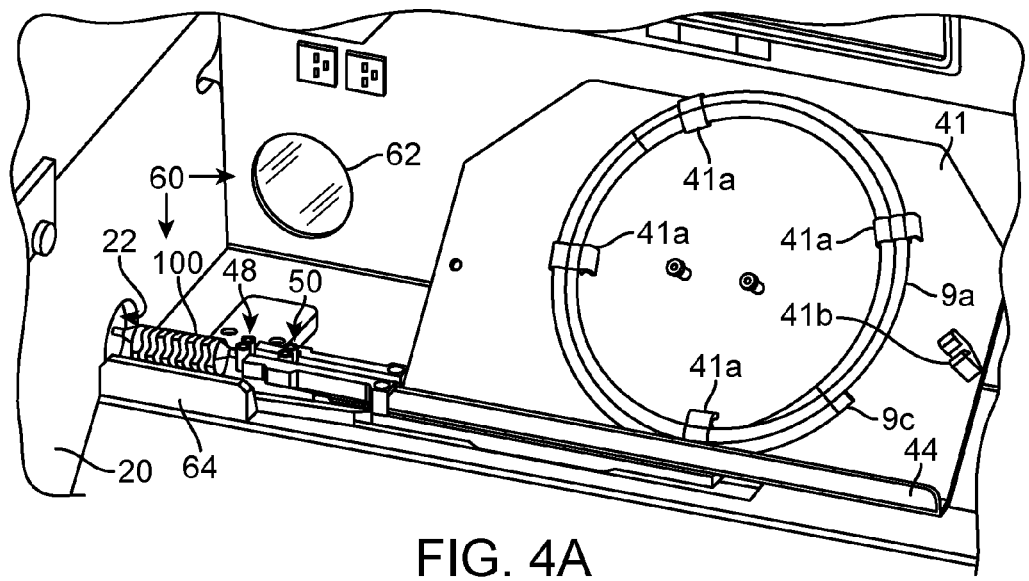
FIGS. 4A-4B are close-up views of a positioning and alignment system for the right hand side station of the system of FIG. 2. Shown are elements of an imaging system and a carriage associated with a positioning and alignment system.
Figure 4B:
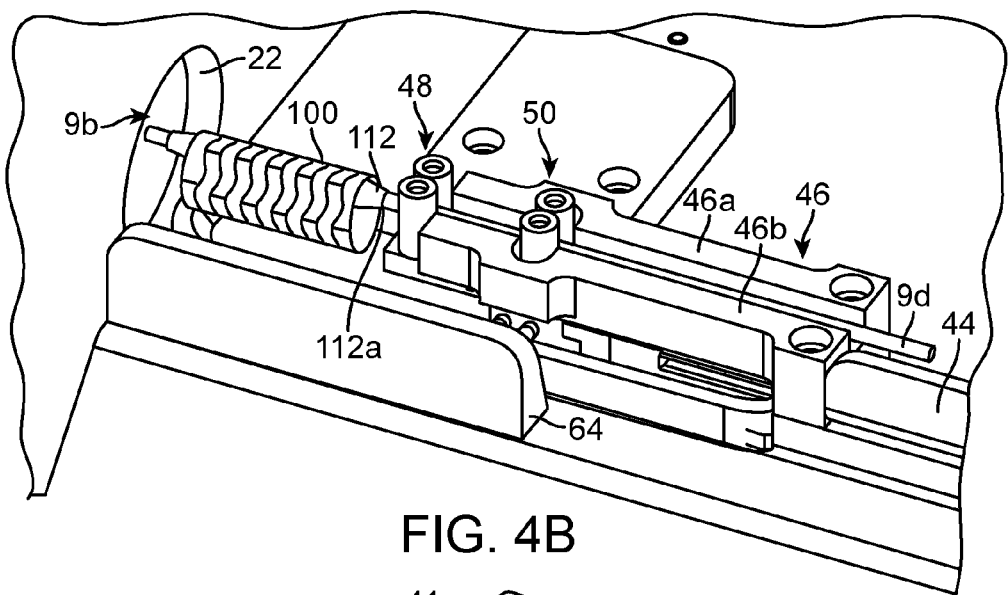

Station 16 includes a carriage 42a (hereinafter carriage 42 or 42a), which carries the stent and catheter into and out of the crimper head 20 and assist with re-aligning the stent 100 on the balloon 112. The carriage 42 translates left and right by a computer-controlled, linear drive mechanism coupled to the carriage 42. Referring to FIGS. 4A-4B there are two close-up perspective views of right positioning and alignment station 16, in particular, the carriage 42 and elements of an imaging system 60 (a camera 62 and reference plane 64) which are used with the carriage 42 to assist with aligning the stent 100 on the balloon 112. The carriage 42 includes a tray 41 for holding a coiled portion 9a of the catheter 9 (via clips 41a). The tray 41 includes a proximal guiding flange 44 which directs the catheter 9 shaft towards fore and aft grippers 48, 50 disposed adjacent a channel 46 for holding the distal end 9b of the catheter 9 in alignment with the entrance 22 to the crimper head 20. The proximal end 9c of the catheter 9 is disposed in a convenient position on the tray 41 to attach a luer extension, which provides a coupling for connecting a pressure source (not shown) and associated pressure gauge to the distal catheter end 9c. The pressure source and gauge are placed in fluid communication with the balloon inflation lumen for inflating and measuring balloon pressure when the stent-catheter assembly is within the crimper head 20. A clip 41b is provided for attaching a hose, which couples to the luer extension.

The carriage 42 channel 46 includes an outer channel piece 46b and inner channel piece 46a, arranged to form parallel walls for alignment of the catheter 9 shaft 9d with the crimper head 20 entrance 22. The distal gripper pair 48 and proximal gripper pair 50 include a pair of opposed posts each receiving a compliant sleeve that abuts the catheter shaft. The distal grippers 48 are fixed in position and spaced apart to provide a snug space for the catheter distal end 9b. The proximal gripper pairs 50 are movable towards and way from each other by a pneumatic actuator to secure and release, respectively, the distal catheter shaft 9d from the channel 46. A user toggle switch (not shown) releases or engages the grippers 50 with the catheter shaft 9d. The grippers 50, therefore, operate as a clamp to hold the catheter 9 distal end 9d within the channel 46. The catheter 9 is positioned in the carriage 42 so that the balloon 112 is forward of the distal grippers 48. The stent 100 is on the balloon 112 in FIGS. 4A-4B. As an aid in alignment a metal rod (not shown) is advanced through the catheter guide wire lumen to increase the catheter's flexural rigidity at the distal end. The channel 46 includes a V-groove formed by a magnetic material, or having a magnetic material proximate the groove to bring the catheter into alignment within the groove and retain it in this position by magnetic forces acting on the rod disposed within the guidewire lumen.

The stent 100 may be manually placed on the balloon 112 by the operator after the balloon 112 has been positioned distal of the grippers 48. After the balloon 112 and stent 100 have been properly located on the carriage 42 distal of the grippers 48, the toggle switch is depressed to bring the proximal gripper pair 50 together to clamp the catheter 9 in place. In another embodiment, the stent may be placed on a tray and the catheter (held on the carriage 42) advanced through the stent bore by a computer-controlled actuator. This stent tray may have a curved receiving surface, e.g., a portion of a cylindrical surface, to receive the stent, which allows the operator to simply drop the stent onto the receiving surface where the receiving surface naturally causes the stent to come to rest at the center, e.g., stent bore axis and axis of cylinder lie in same plane. A flange may be formed along the distal edge of this receiving surface so that the stent abuts the flange if the stent is displaced distally. The catheter distal end is advanced into the stent bore until the distal balloon marker begins to appear distal of the stent distal end. If there is contact between the catheter and stent during this step, the distal flange will act as a stop to hold the stent in position while the catheter distal end is passing through the stent bore. In another example the tray depicted in FIG. 6 and described more fully below may receive the stent. Then the catheter distal end is advanced through the stent bore. In either of the above embodiments, e.g., tray of FIG. 6 or body having a curved receiving surface, the stent alignment process (as described in greater detail below) may be performed concurrently with placing the stent on the distal end of the catheter.

Figure 4C:
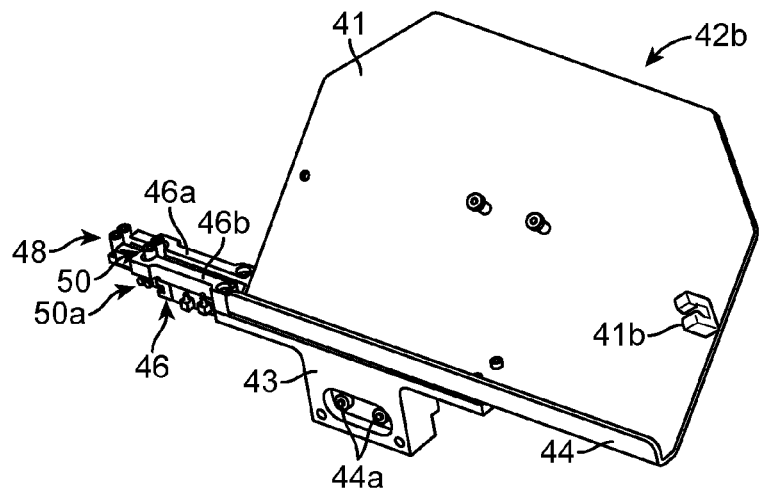
FIG. 4C is a perspective view of the carriage portion of the positioning and alignment system of FIG. 2.

FIG. 4C shows a perspective of the carriage 42. As mentioned above, carriage 42 includes a tray 41 with guiding flange 44, rail 46 and clip 41b, and grippers 48, 50. In FIGS. 4A-4B carriage is shown being received within a slot which it translates along as the stent-catheter assembly is moved towards/away from opening 22. Carriage 42 includes an extension piece 43 received within the slot and connected to a linear actuator via bolts 44a. Grippers 50, which are pneumatically actuated, are connected to the actuator via couplings 50a.

A laser light (or camera) may be used to assist the operator with identifying the appropriate position of the balloon 112 aft seal 112a relative to the distal gripper pair 48, to ensure that the balloon 112 and stent 100 will be advanced to the designated area within the crimper head 20 prior to activating the crimper head 20. If the catheter distal end 9b is too far forward of, or close to the gripper 48, which is arbitrarily chosen, for convenience, as the reference point for the travel length forward of the carriage 42 from the position shown in FIG. 4A to a crimping location within the crimper head 20, then the stent and catheter can be positioned incorrectly within the crimper head 20, resulting in possible damage to the stent and/or the crimper head. The operator adjusts the position of the catheter distal end 9b relative to the laser light, which is directed at, and generates a red line across the catheter shaft, until the balloon 112 proximal seal 112a is illuminated by the light. This laser light is directed about 10 mm forward of the grippers 48.

As mentioned earlier, the carriage 42 and imaging system 60 assist with aligning the stent on the balloon. As shown in FIG. 4A, the catheter balloon 112 and stent 100 are located between the reference plane 64 and the camera 62 (the reference plane provides a black backdrop, or contrasting background to the stent and catheter so that images collected by the camera 62 can clearly discern the stent and balloon 112 distal and proximal seals, and/or balloon markers). The background may be any color or may consist of another light source to backlight the product if desired for accurate dimensional transitions.

Reference points may be disposed on the backdrop or contrast surface, e.g., an approximate distal and proximal location for the balloon on the catheter when the balloon has properly positioned on the rail by the operator, or reference indices indicating a measure of length, e.g., hashes showing millimeter increments.

After the catheter 9 is positioned in the carriage 42 as shown in FIG. 4A, stent 100 alignment on the balloon 112, followed by the crimping sequence may be initiated by an automated process. Thus, following proper placement of the catheter 9 within the carriage 42, the remainder of the crimping process for the stent 100 and catheter balloon 112 may commence without further involvement by the operator.

Misalignment of the stent on the balloon may be detected using the imaging system 60 and computer-executed algorithm that includes a position detection routine that collects digitized image(s) of the stent 100 on the balloon 112 and analyzes the image(s) to determine whether the stent is aligned or misaligned. That is, collected image(s) is/are analyzed to locate edges 104, 105 of the stent relative to the balloon 112 (see FIG. 5A). To assist with identification of stent edges, balloon seals, stent and balloon markers etc. from the images data about the stent is accessed. Stent and balloon lengths, distances from edges to markers, etc. and other identifying characteristics may be remotely accessed through the stent ID then compared to the image to identify (through pattern recognition routines) the stent structure used to determine whether the stent is misaligned relative to balloon markers 114.

After a determination has been made that the stent is misaligned, a positioning mechanism is employed to automatically reposition the stent 100 on the balloon 112. The computer algorithms that may be used to re-align the stent include a controller with or without a feedback loop. In both instances, the controllers seek to move the stent by a computed offset distance to properly align the stent between balloon markers.

Figure 5A:
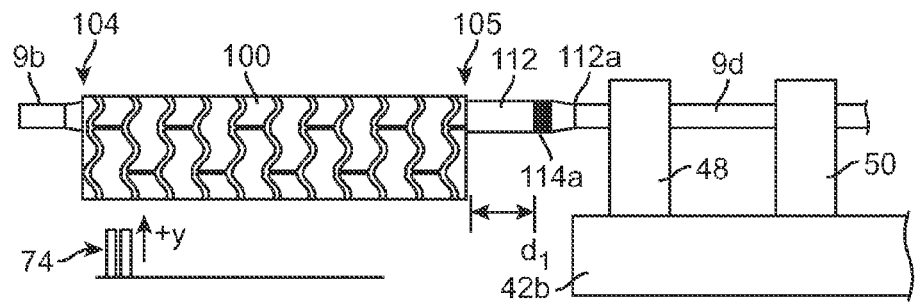
FIGS. 5A-5C is a sequence of views showing a re-positioning/re-alignment of a stent on a balloon. The sequence shown uses computer-controlled actuator portions of the positioning and alignment system.

For example, referring to a controller without feedback, after locating the stent edges 104, 106, balloon seals 112b, 112a and/or marker bands 114a, 114b in the image, the stent 100 position relative to the balloon markers can be found and an offset distance "d1" computed (FIG. 5A). This offset is then input to the controller that has control over movement of carriage 42 and/or stent 100 to move one relative to the other. After the balloon 112 has been displaced relative to the stent 100, or the stent 100 displaced relative to the balloon 112, presumably by the distance d1, a second image is taken to re-evaluate the stent position relative to the balloon 112. The same sequence may be performed multiple times until the stent 100 is properly located on the balloon 112, e.g., between marker bands 114a, 114b. Movement of the stent relative to the balloon is determined once the offset d1 is computed. If the second image reveals that the stent is still misaligned, a new offset d1 is computed and the process is repeated.

Examples of actuator-controlled mechanisms that may be incorporated into station 16 for restraining or moving the stent relative to the balloon 112 (or balloon relative to stent) are depicted in FIGS. 5A-5C, FIG. 6 and FIGS. 7A-7B.

Figure 5B:
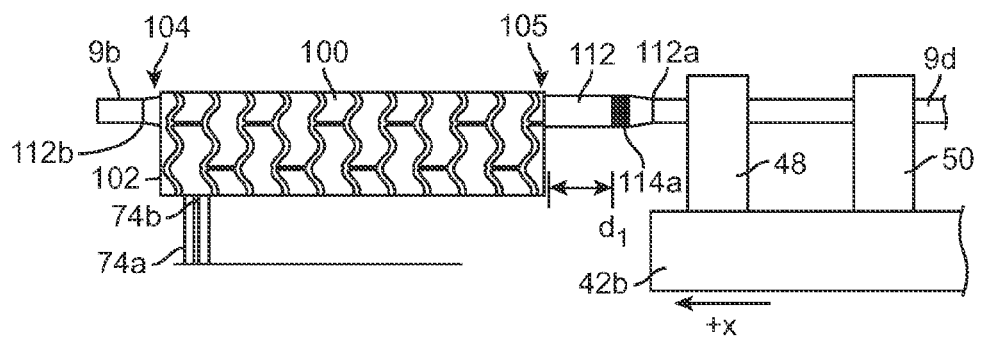
Figure 5C:
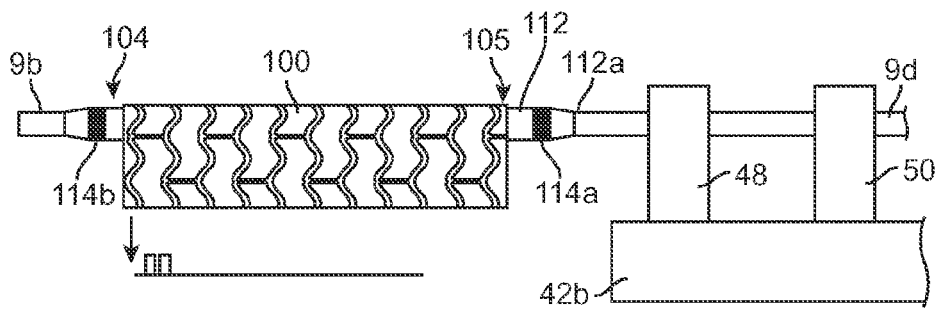

Referring to FIGS. 5A-5C, located beneath the stent 100 is an arm or pair of arms 74 that are raised (+y) to engage struts or ring elements of the stent 100. Shown is one pair of arms 74 at end 104 of stent 100. The arms 74a, 74b are positioned between a stent strut and then brought together to grip the strut or ring element 102 (FIG. 5B). Or the arms 74a, 74b may be positioned between struts and then moved apart until then contact a stent ring element or strut. Two pair of arms of the type shown (i.e., arms 74), operated simultaneously, may restrain both ends 104 and 106 of the stent, or one arm (or post) at each end 104, 106 may be raised (+y) to serve as an abutment preventing horizontal motion (+/−x) of the stent 100 relative to the balloon 112 so that the balloon 112 may be moved relative to the stent 100. Referring to FIGS. 5B-5C, the carriage 42, for example, is moved forward by the distance d1 while the stent is held by the arms 74. After the carriage 42 is moved, the arms 74 are retracted to their starting position. A second image of the stent 100 and balloon 112 is taken to determine whether the stent 100 is now located between the marker bands 114a, 114b as shown. Referring of FIG. 6, a cradle 76 having a plurality of upwardly disposed protuberances 77 (e.g., square-like extensions, bumps) or roughened (rubber like) surfaces 77 having a high coefficient of friction may, in the alternative, be used to restrain stent 100 motion while the balloon 112 is repositioned. Alternatively, the cradle 76 may be moved horizontally (−x) to move the stent 100 relative to the balloon 112. This tray 76 may also be used to place the stent 100 on the catheter 9, as mentioned earlier.

Figure 7A:
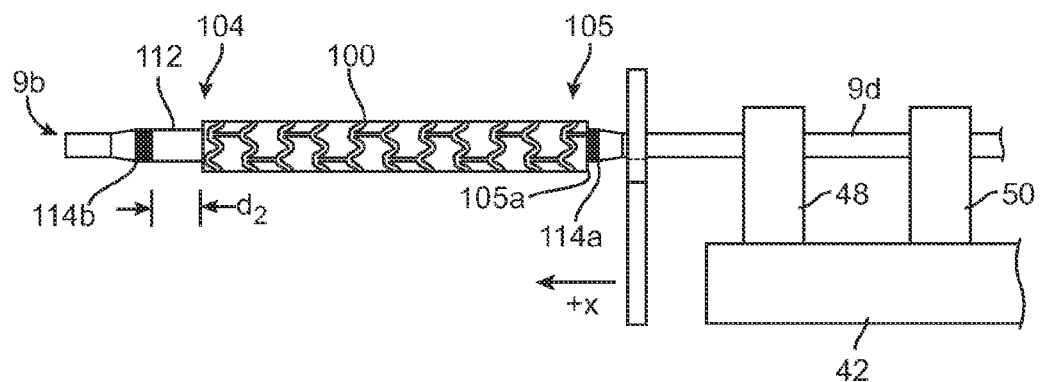
FIGS. 7A and 7B depict aspects of another example of a mechanism of a computer-controlled positioning and alignment system. In this example, a polymer stent is being repositioned after the stent has been pre-crimped to a smaller diameter
Figure 7B:
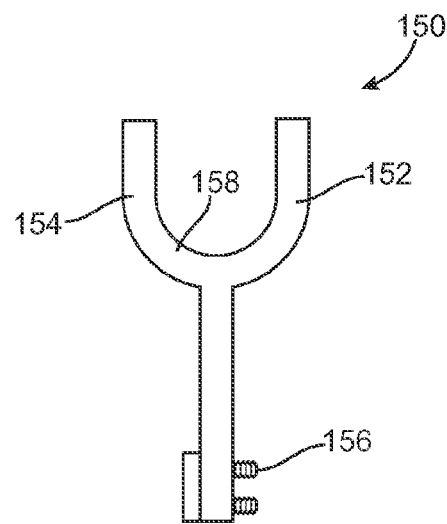

Referring to FIGS. 7A-7B there is another embodiment of a stent alignment mechanism. Shown is stent 100 after its diameter has been decreased to about ½ size of its starting diameter following a pre-crimp step, discussed in greater detail, below. A fork 150 shown in FIGS. 7A, 7B is used to engage the stent 100 proximal end 105b to push the stent 100 forward over the balloon 112 until the ends 104, 105 are between the balloon markers 114. The fork 150 is prepositioned adjacent the carriage 42, then moved forwards by a linear actuator. The fork 150 includes opposed arms 152, 154 extending upwards from a root. Connecting hardware 156 for connecting the fork 150 to an actuator arm (not shown) is shown. A inner surface 158 of the fork 150 is shaped to as a rounded surface and sized so that there is a slight clearance between the balloon surface and the surface 158. Thus, as the fork 150 moves to the left in FIG. 7A the surface 158 passes over the outer surface of balloon 112 and when reaching the stent 100 fork 150 abuts the end 105a. The fork 150 and stent 100 continue to move distally over the balloon 112 according to the controller logic (below) until the stent 100 has moved the offset distance d2 indicated in FIG. 7A.

In the case where the stent 100 being located to far distal, i.e., edge 104 is distal of balloon marker 114b, then a similar fork 150 may be disposed to the left of the stent to push it towards the proximal balloon marker. The same fork 150 may be used for correcting distal or proximal misalignments. The fork 150 may be re-positioned distal or proximal of the stent 100 depending on the alignment Correction needed. When alignment is needed, it can be preferred to have misalignment always be of the type illustrated in FIG. 7A, since in these cases the catheter is brought into tension, rather than into compression, when there is stent-balloon interference as the stent 100 is moved relative to the balloon 112.

As indicated earlier, prior to a pre-crimp, a polymer stent diameter is can be much larger than the balloon 112 diameter (FIG. 5A). For re-alignments at this stent diameter, it should not make much difference whether there is a proximal or distal re-alignment needed to the left or right needed since the stent 100 easily moves over the balloon 112. However, when re-alignment is needed following a pre-crimp step (FIG. 7A), where the polymer stent diameter has been reduced to a point where it begins to engage the balloon surface, there is expected to be stent-balloon interaction to some degree. This follows from the purpose of the pre-crimp diameter. The diameter is chosen so that the stent does not easily move about, yet is still capable of being moved relative to the balloon surface when a re-alignment is needed. As alluded to earlier, this highlights another challenge faced with polymer stents not present with metal stents. A large starting diameter is used for a polymer stent, as mentioned earlier, for mechanical performance reasons at the deployed diameter. However, the larger diameter (relative to the balloon) also increases the likelihood the stent will shift relative to the balloon when the initial diameter reduction is performed. There is a need, therefore, to remove the stent after an initial diameter reduction to verify that it is properly aligned before the stent is reduced to a diameter that prevents further adjustment.

When the stent is misaligned relative to the balloon markers as shown in FIG. 7A, the stent is pushed forward. Any resistance to stent movement by stent-balloon contact will produce tension in the catheter, which is acceptable. However, if the stent 100 is disposed distal of the distal balloon marker and needs to be re-aligned proximally, resistance to movement by balloon-stent contact will place the catheter distal end 9b into compression, which can cause the tip of the catheter to displace off axis, makes the re-alignment process more difficult (since the catheter is moving laterally while the stent is being repositioned).

Figure 6:
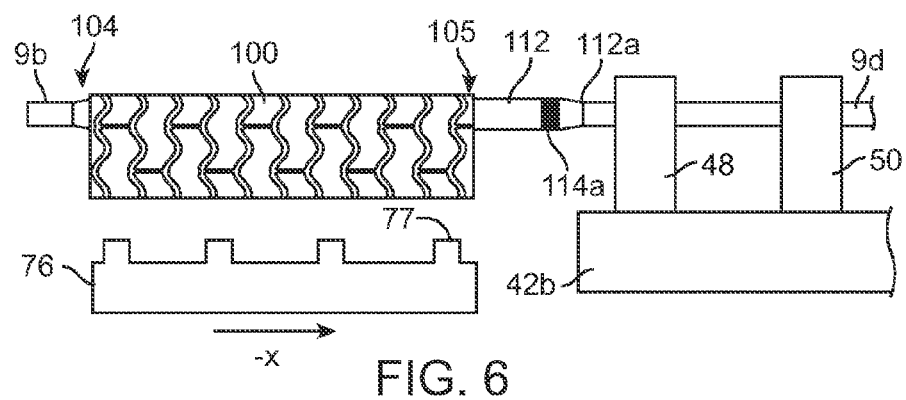
FIG. 6 is another example of a mechanism of a computer-controlled positioning and alignment system.

This problem may be addressed by holding the distal end 9b while the fork 150 is moved towards the proximal end, or by using an alternative mechanism (as necessary) to grip and move the stent while holding the distal tip on axis as the stent 100 is being moved. For example, in an alternative embodiment the upper surface of tray 76 from FIG. 6 is curved, or includes a pair of opposed curved surfaces that are brought together to grip the surface of the stent 100, then this tray is displaced to the proximally while the tip 9d is held on-axis. Alternatively, the initial alignment of the stent 100 can be proximal of the proximal balloon marker, thereby ensuring that any shifting during the pre-crimp will not result in the stent 100 being distal of the distal balloon marker.

The sequence of operations described above, which makes use of one or more computer-controlled actuating mechanisms, are controlled by a computer, e.g., a personal computer or PC or workstation having DRAM, disk storage, hardware bus, CPU, user input device, e.g., touch screen 16a, keyboard, mouse, external drives, and a network connection to a LAN and drivers for controlling the actuators used to drive the mechanisms described in FIGS. 5-6. The computer resident at station 16a may access information about the stent and catheter remotely using a LAN, WAN or other network type, which information may be accessed through a file server. The machine executable code associated with the algorithmic aspects of the positioning system may be software or hardware implemented, or a combination of both. Off the shelf equipment may be used for the imaging system 60 and actuators referred to above.

Determining a location of the stent edges 104, 105 and balloon distal/proximal seals 112, 114 from the camera 62 collected image(s), may be accomplished using pattern recognition algorithm, which, as mentioned earlier, can compare the camera 62 image to pre-stored information about the stent length and/or pattern to distinguish the stent 100 from the balloon 112 in the image. Distinguishing balloon markers, for example, from the stent and other parts of the catheter 9 may be accomplished by illuminating the stent and balloon with light that causes the balloon markers to illuminate light within a particular band in contrast to the surrounding image. The same technique may also be used to find the stent edges, based on the illumination of stent markers then computing the location of the stent edges relative to those markers. The pattern recognition algorithm may be programmed to receive as input the stent length, marker location and pattern, pre-crimp diameter, balloon length between proximal/distal seals and markers and output a signal to indicate the stent is aligned with the balloon or the offset distance, which is then received by the controller for repositioning the stent 100 relative to the balloon 112.

As mentioned earlier, a controller using a feedback loop may be used to reposition the stent on the balloon. The feedback for this controller would be position information extracted from images of intermediate positions of the stent relative to the balloon as the stent or balloon is moved relative to the other. Thus, the stent, for example, is moved an incremental distance and an image is taken of the new position. The next input to the actuator, e.g., an input to a servo, is computed based on feedback information extracted from the image, the next incremental displacement is performed, a third image is taken, etc. until the offset distance approaches zero, i.e., the stent is between the balloon markers. The control system may adopt a PID control, or state-space control logic for computing the next input to the actuator. The actuators may be controlled by a servo mechanism or stepper motors to provide precise control over movement of the actuators.

It would, of course, be desirable to utilize a process that does not require an iterative closed or open-loop feedback control for locating a stent between markers. Multiple iterations, however, may be necessary when a stent is repositioned following pre-crimp, for the reasons alluded to earlier. When re-alignment is needed following pre-crimp the balloon may introduce enough hysteresis into the system to require an iterative approach.

As discussed earlier, pre-crimping of the stent seeks to provide enough friction to not cause the stent to easily move about, but not too much friction to prevent repositioning when needed. The pre-crimp reduces the diameter to enable more accurate measurement of the distance between the stent edge and the marker band. The majority of defects and stent movement due to distortion of the stent occurs during a pre-crimp step. In this sense it will be appreciated that by incorporating aspects of the disclosed alignment system following pre-crimp there is the opportunity to make fine adjustments of the stent when it is very close to its final diameter and shape.

Figure 8:
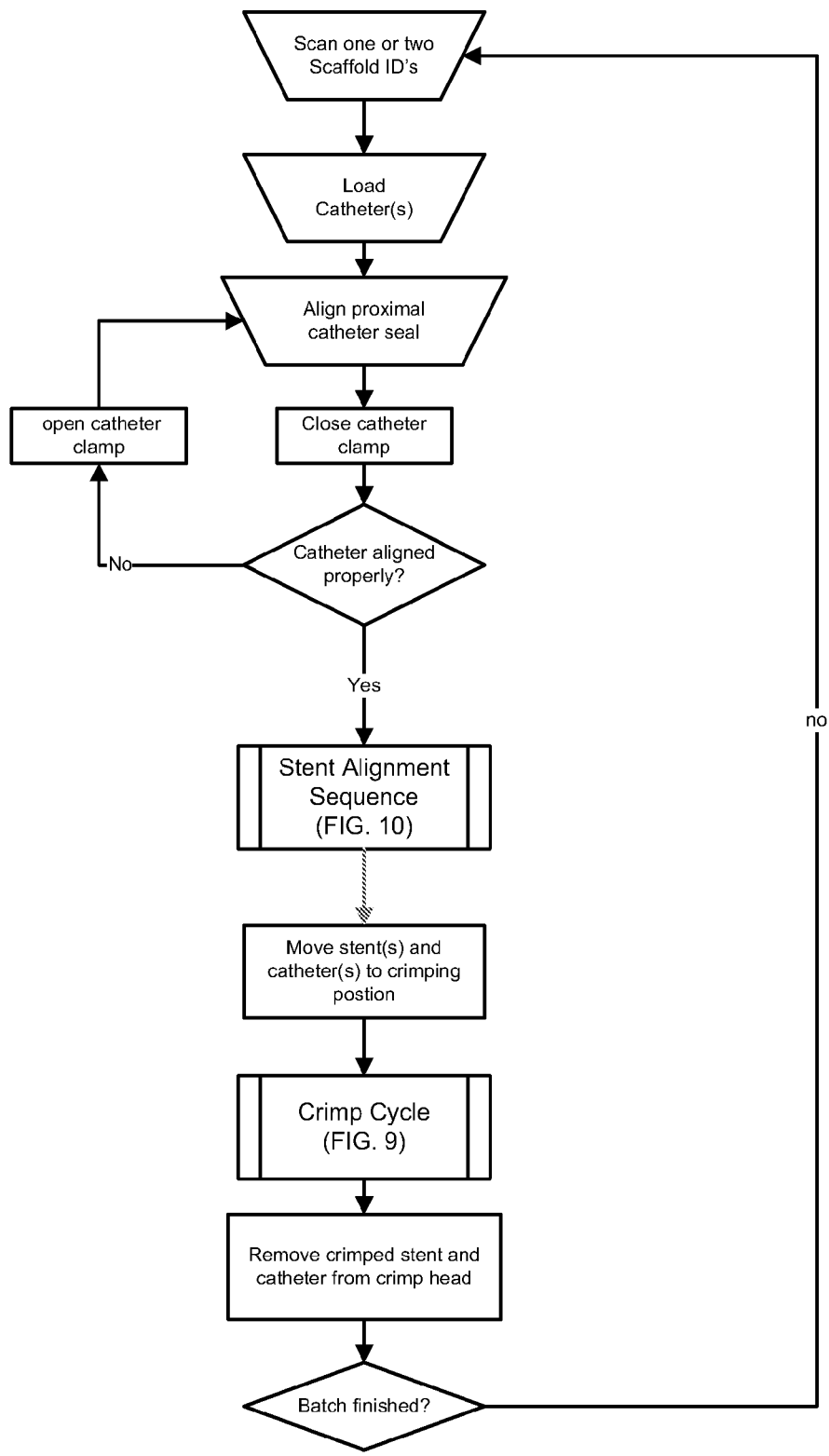
FIG. 8 is a flow process describing steps associated with the positioning and alignment of a stent-catheter assembly, and then crimping the stent to the catheter using the system of FIG. 2.
Figure 9:
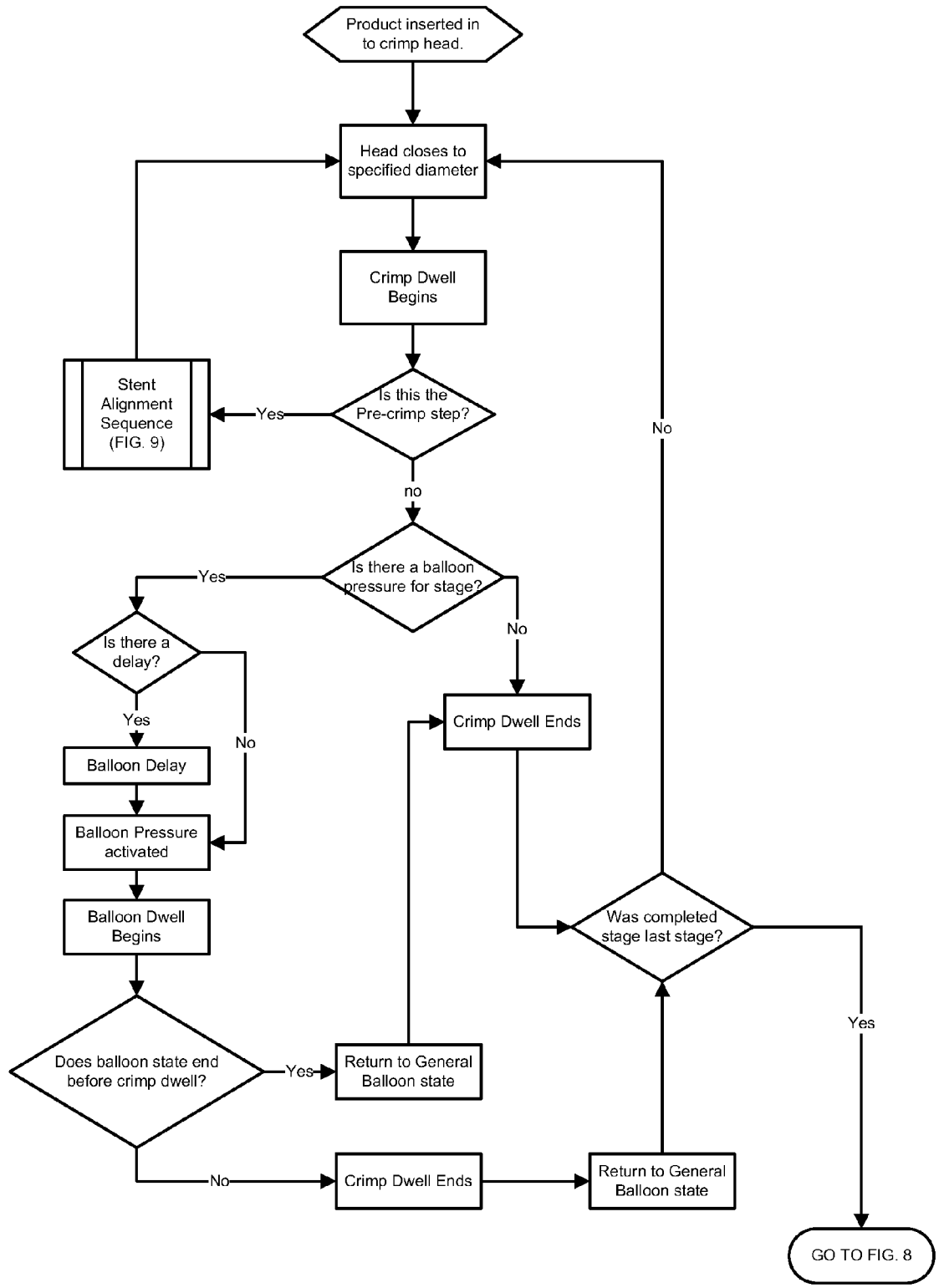
FIG. 9 is a flow process showing steps associated with crimping a polymer stent to a catheter balloon.
Figure 10:
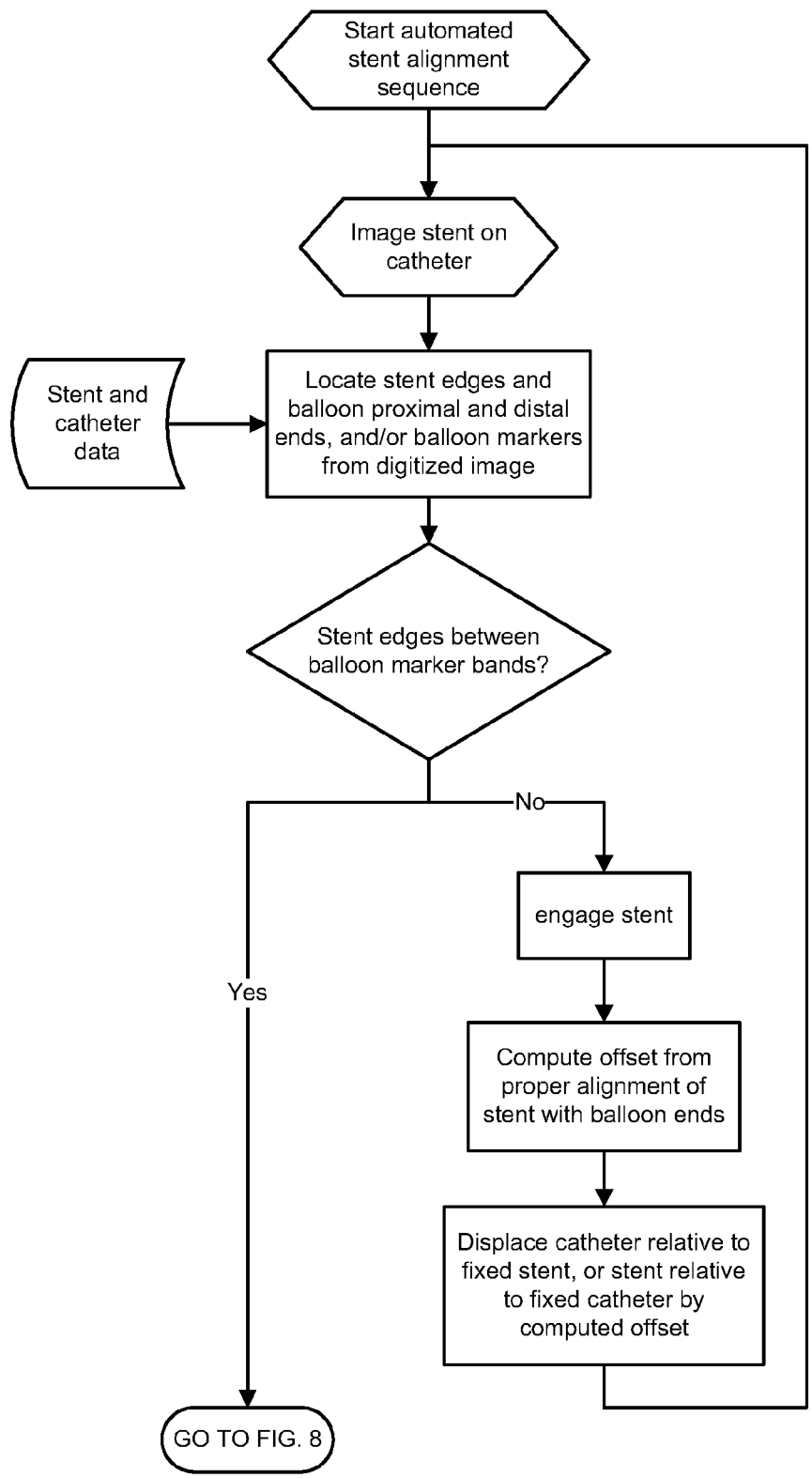
FIG. 10 is a flow process describing a process for verifying alignment of the stent on the balloon and repositioning the stent on the balloon to correct for a misalignment of the stent on the balloon.

FIGS. 8-10 describe process flows for positioning and aligning a catheter and stent and crimping the stent in the crimper head 20 using the system 10.

Referring to FIG. 8, the process begins by an operator reading the identification (ID) of the stent(s) to be crimped to a catheter. The process of positioning, aligning and then crimping is the same for a stent and catheter loaded at the left or right stations 14, 16 of the system 10. When both stations 14, 16 are being used to simultaneously crimp stents to catheters 8, 9, a central processor may control both stations, or a separate processor at each station 14, 16 may control the process up until the point the stents and catheters are ready to be inserted into the crimper head 20, at which point a central control takes over for the crimping steps. One aspect of the crimping process, a pre-crimp step, is followed by removal of the stent and catheter to verify alignment. For this step control may return to the station 14, 16 processor to perform a verification and possible re-alignment, followed by return of control over to a central processor (or only one station 14, 16 processor performs the crimping sequence while the other remains idle).

Referring to the process flow of FIG. 8, with the stent ID input to the computer control, process controls are selectable by the operator via the user display 16a, or these controls may be automatically retrieved from storage base d on the input stent ID. The catheter 9 is then loaded onto the alignment carriage 42. The coiled portion 9a of the catheter 9 is placed onto the tray 41. This is a manual operation performed by the operator. The catheter proximal end 9c is positioned to face the clip 9c, the coiled portion 9a is placed on the tray 41 and the shaft 9d including proximal end 9b is aligned via the rail 44 and positioned distal of the grippers 48. A luer extension is attached and the pressure source connected to the luer extension. The operator depresses a button to bring gripper pairs 50 together, thereby clamping the catheter in the carriage 42. The position of the balloon 112 proximal seal 112a relative to the distal grippers 48 is then verified by inspecting whether an illuminating light shines on the balloon proximal seal location (or a camera verifies a proper location and indicates this position by a green light, or red light if misaligned). If properly aligned, the flow next proceeds to the stent alignment sequence (FIG. 10), if not, the clamp is released and the operator re-positions the catheter distal end 9b until the aft balloon seal aligns with the reference light. The stent may be placed on the catheter manually or by an automated mounting process, as explained earlier.

Referring to the process flow of FIG. 10, with a signal received from the operator, e.g., a start button depressed, to begin the crimping sequence, control then shifts to the stent alignment phase (or stent placement on balloon and alignment phase using the same mechanism and control system) for determining whether the stent is properly aligned relative to the balloon markers. The positioning carriage 42 advances the catheter distal end 9b and stent 100 to the appropriate position for checking the alignment, i.e., the stent and balloon being centrally positioned at the camera 62 bore site. In this position, images collected by the camera may be used to extract distance information, relative positions of the stent and balloon and making adjustments to the stent position as described earlier.

After collecting one or more digital images, stent and catheter information is recalled to assist with determining the exact location of the stent edges and balloon markers and/or seals. For example, the distance from the distal balloon seal and balloon marker may be used to determine where the distal balloon marker is located relative to the distal seal, as in the case of the stent edge overhanging the balloon marker, thereby obscuring the camera 60 view of it (FIG. 5A). With information about the length of the stent, its pre-crimp diameter, stent pattern, location of its markers relative to edges, etc. the identification of the markers in the digital image, or other patterns matched to the information from the image the algorithm may determine where the stent edge is located.

With the stent edges and balloon markers located, the controller (with or without a feedback loop) determines whether the stent is aligned, or whether the stent or balloon needs to be moved relative to the other so that the stent is between the balloon markers (as desired) prior to crimping. If the stent is aligned between the balloon markers, then a control signal is passed to the central control to have the stent and balloon moved into the crimper head 20. If it is determined that the stent is not aligned, then the stent is moved relative to the balloon (or balloon relative to the stent) using, for example, the mechanisms described in FIGS. 5-7. After the stent has been aligned with the balloon markers, the stent and catheter are now ready for crimping.

There are two possible stent positioning sequences that would occur during the crimping process. The first would include the pre-positioning of the non-crimped stent on the catheter relative to the marker bands. It may be preferred during the initial alignment phase to instead bias the stent proximal to the desired location, such that the final positioning after pre-crimp would always be done by pushing the stent distal relative to the catheter and thus putting the catheter into tension, rather than compression. The second possible positioning sequence would include the re-positioning of the stent on the catheter after pre-crimping, before final crimp. This needs to be the final location as the stent cannot be moved relative to the balloon after final crimping.

Referring to the general process flow for crimping of FIG. 9, the carriage is advanced forward into the crimper head 20 under computer control to ensure the stent does not shift when being placed within the crimper. The first diameter reduction by the crimper, called a pre-crimp, reduces the stent diameter by about ½. As indicated above, stent struts have not been pressed into the balloon material, but have begun to engage this material. After the pre-crimp, the stent and balloon are removed from the crimper head 20 so that the stent 100 position relative to balloon markers may be verified once again before the final crimp begins. Control then switches over to the process described in connection with FIG. 10. After that process again signals that the stent is aligned properly with the balloon, the stent and balloon are again placed within the crimper head 20. The final crimping steps begin. Examples of these crimping steps for a preferred embodiment, a PLLA stent crimped at a temperature near its glass transition temperature and reduced to a diameter of about 2.5 times that of the pre-crimp diameter, are shown in FIG. 11.

One or two forms of heating may be employed during the crimping process. Heating may be accomplished by heating the jaws of the crimper head, or heated air may be used in addition to heating the crimper jaws. There may be a benefit to using both heated air and convection and radiation from the crimper jaws. This combination of heat sources can cause the balloon material to flow more easily into the gaps between stent struts. Additionally, the use of hot air concurrently with heated jaws will reduce the temperature needed to heat the stent and balloon through convection and radiation from the jaws. This can be desirable so that the surface of the stent does not overheat and cause damage while being crimped. Thus, by using air in combination with heated jaws the jaw temperature can be lowered.

Figure 11:
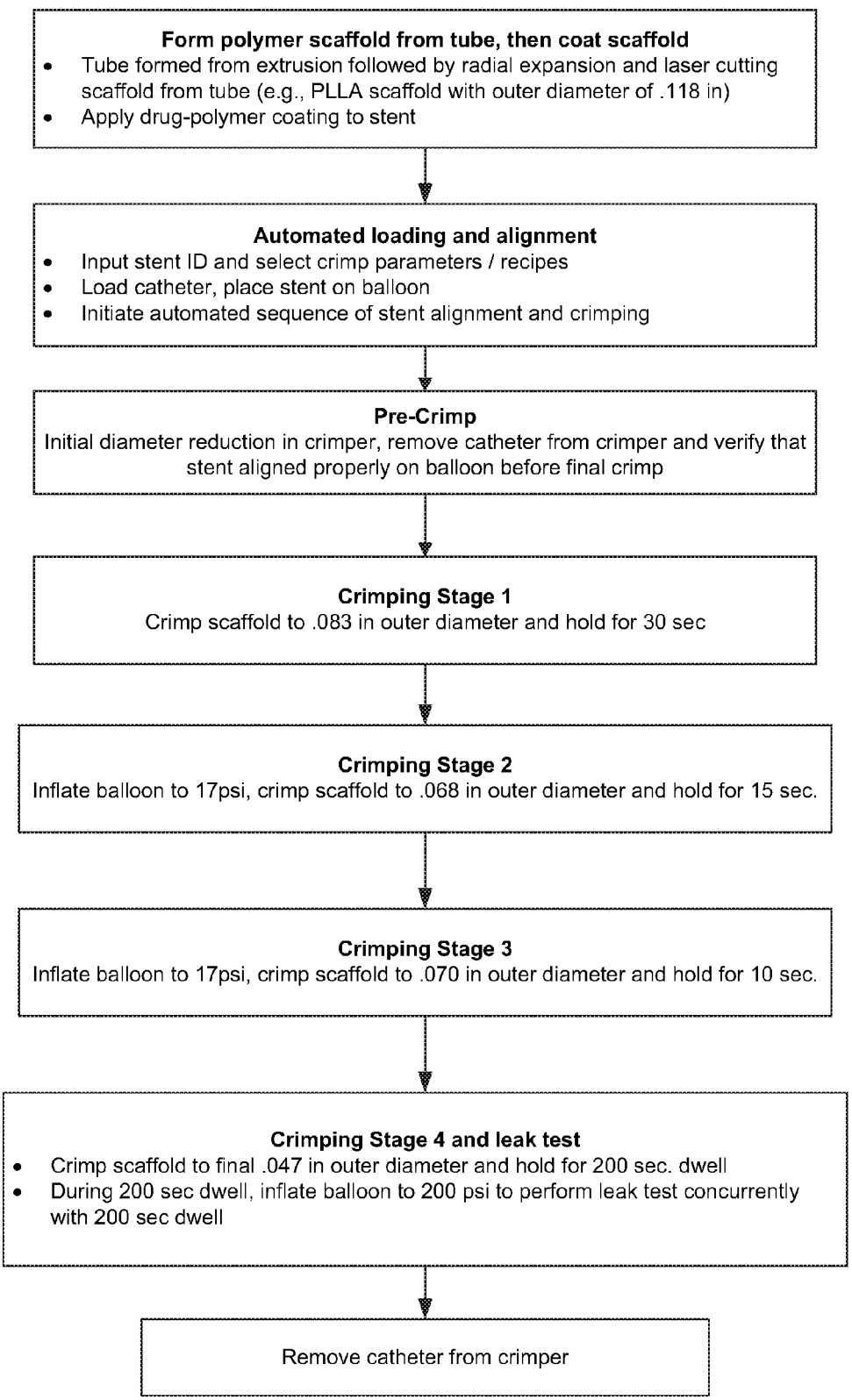
FIG. 11 is a flow chart showing some of the manufacture steps associated with making a PLLA stent and then crimping the PLLA stent to a catheter balloon.

As can be appreciated from FIG. 11, there are several intermediate crimping steps, with significant dwell times needed for the polymer stent. This is because unacceptable cracks can develop if the diameter is reduced at too high a rate. A slow, incremental crimping process is needed so that internal stresses can work themselves out. Ideally, from a strength/integrity point of view a polymer material should be plastically deformed at an extremely slow rate (e.g., over several hours). However, this is not practical from a production viewpoint. The crimping steps illustrated in FIG. 11 were found to produce acceptable yields. When considering the significant time needed to perform a crimping sequence for a polymer stent as shown in FIG. 11, the advantages of an automated system 10 are appreciated.

The final crimp step, i.e., crimping stage 4 from FIG. 11, includes a 200 second dwell time. While the crimper jaws remain fixed in this position on the stent struts (for stress relaxation and minimizing recoil after the jaws are removed from the stent) the balloon is inflated to a pressure of about 200 psi to perform a leak test. After the leak test and 200 second dwell, the stent and catheter are removed from the crimper, a sheath is placed over the stent, and the stent and catheter are placed in a refrigeration unit. It has been found that there are benefits, in addition to the reduction in the time needed in the production process, to performing the leak test while the polymer stent is in the crimper head and restrained by the crimper jaws during the dwell time. First, by increasing the balloon pressure while at an elevated temperature, the balloon-stent contact can be increased as the increased pressure causes balloon folds to find their way between stent struts. This can increase the retention force of the stent on the balloon. Second, a lower stent-balloon profile is possible.

Figure 1A:
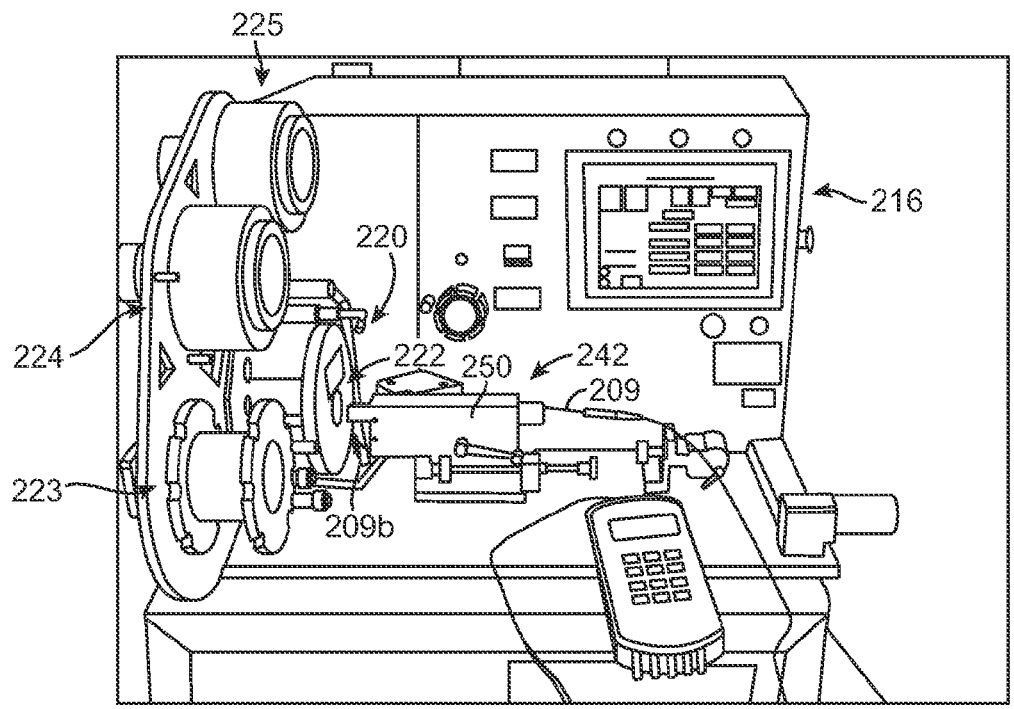
FIG. 1A is a perspective view of a crimping system according to the prior art.
Figure 1B:
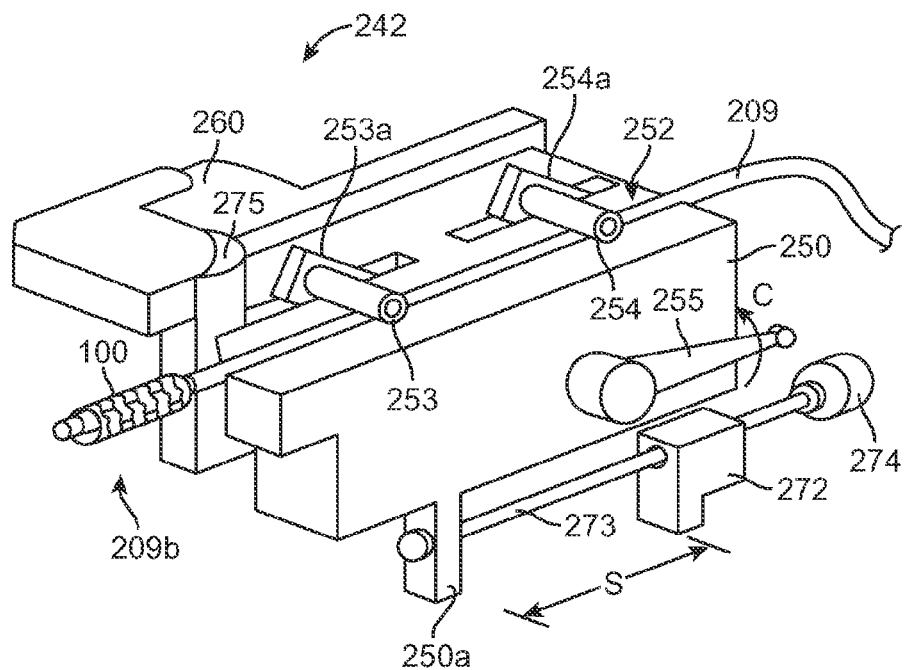
FIG. 1B is a perspective view of a carriage of the system of FIG. 1A.

In the typical case, such as when using the apparatus of FIGS. 1A-1B, the leak test is performed after the stent has been removed from the crimper head and inserted within the restraining sheath. The restraining sheath, being far more radially compliant than the crimper jaws, will expand to some degree when the leak test is performed. It is preferred to maintain the smallest profile as possible. Thus, if the leak test is performed in the crimper head, the smaller profile is maintained since the crimper jaws will maintain the diameter despite the increase in balloon pressure.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the scope of this invention.

What is claimed is:

1. An apparatus, comprising:
   a crimper head having jaws and a non-stick material arranged for being placed between the jaws and a stent received within the crimper head;
   a first station and a second station disposed adjacent the crimper head and configured to receive, respectively, a first stent and a first balloon catheter assembly and a second stent and a second balloon catheter assembly;
   the first station and the second station each include an aligning portion and a positioning portion; and
   a processor for simultaneously crimping both the first stent to the first balloon catheter and the second stent to the second balloon catheter using the crimper head,
   whereupon receiving a user command, the processor causes
   (a) the first station to align the first stent with the first balloon catheter and the second station to align the second stent with the second balloon catheter using the respective first and second station aligning portions,
   (b) the first station to insert the first stent and first balloon catheter into the crimper head and the second station to insert the second stent and second balloon catheter into the crimper head using the respective first and second station positioning portions, and
   (c) the crimper head to perform a crimping sequence for crimping both the first stent to the first balloon catheter and the second stent to the second balloon catheter.

2. The apparatus of claim 1, wherein the crimper head includes a compliance adjustment device for adjusting the travel of jaws within the crimper so that only one stent and catheter can be crimped at a time, or two stent-catheter assemblies can be crimped at the same time.

3. The apparatus of claim 1, whereupon the processor is further configured to perform a leak test for both the first balloon catheter and the second balloon catheter while the jaws are applying a force to the first stent and second stent disposed within the crimper head.

4. The apparatus of claim 3, wherein the first stent and second stent are polymer stents.

5. The apparatus of claim 4, wherein the first stent and second stent are made from PLLA.

6. The apparatus of claim 1, wherein the aligning portion includes
   a camera for obtaining an image of a stent on a balloon,
   machine readable instructions accessible to the processor for analyzing the image to determine whether the stent is misaligned on the balloon,
   an actuator for displacing one of the stent and balloon relative to the other of the stent and balloon if a misalignment of the stent relative to the balloon was detected from the analyzed image, and
   a controller for controlling movement of the actuator for displacing one of the stent and balloon relative to the other using the actuator according to an offset of the stent relative to the balloon.

7. The apparatus of claim 6, wherein the processor is further configured to cause the positioning portion to automatically advance the stent and balloon into the crimper head when the processor receives a signal from the aligning portion indicating that the stent is aligned on the balloon.

8. The apparatus of claim 7, wherein the positioning portion further includes
   a carriage for supporting a stent and catheter; and
   an actuator for displacing the carriage towards the crimper head, thereby advancing the stent and catheter into the crimper head, upon receiving a command signal from the processor.

9. The apparatus of claim 8, wherein the carriage includes
   a tray for receiving a coiled catheter,
   a channel connected to the tray for aligning the catheter distal end with an opening of the crimper head, and
   a gripper for clamping the catheter to a rail of the tray.

10. The apparatus of claim 8, wherein the positioning portion further includes an optical alignment device for aligning a proximal balloon seal relative to a location on the carriage to ensure that the stent and catheter will be advanced to the proper location within the crimper by the actuator.

11. The apparatus of claim 8, wherein the processor includes a personal computer or workstation resident at one or both of the stations, wherein the personal computer or workstation includes a network connection, a storage medium, a display, an input/output device and software-based device drivers for operating the positioning portion and the alignment portion.

12. The apparatus of claim 1, wherein the processor is configured for automatically accessing crimping parameters that define the crimping sequence, and stent and catheter attributes from a storage area upon receiving an identification code for the first stent and the second stent.

13. A method for crimping a stent to a balloon of a balloon catheter, the balloon having balloon markers identifying a proper alignment of the stent with the balloon, comprising:
   preparing the balloon catheter for crimping including placing the catheter on a movable carriage;
   verifying that the stent is aligned with the balloon including collecting at least one image of the stent and balloon and then analyzing the image to verify that the stent is between the balloon markers;
   after the verifying step, inserting the stent and balloon into a crimper; and
   crimping the stent to the balloon including a first crimping step and a second crimping step,
   the first crimping step including reducing the diameter of the stent to a diameter greater than a fully crimped diameter,
   removing the stent and balloon from the crimper head, then repeating the verifying step including collecting at least one additional image and analyzing the image to verify that the stent is between the balloon markers and if the stent is not between the balloon markers, longitudinally shifting the stent on the balloon to place the stent between the balloon markers, and after repeating the verifying step, re-inserting the stent and balloon into the crimper head and performing the second crimping step.

14. The method of claim 13 wherein the stent is a polymer stent, the crimping step further including a final crimping step whereupon after the second crimping step the polymer stent diameter is reduced to a final crimp diameter, the final crimping step further including a dwelling period wherein jaws of the crimper are fixed in position corresponding to the final crimp diameter for a pre-designated time period after the polymer stent has obtained the final crimp diameter, wherein during the dwelling period the balloon upon which the polymer stent is crimped is inflated to a pressure and then held at that temperature to detect any possible leaks in the balloon.

15. The method of claim 13, the preparing step including a stent mounting step including placing the stent on a second carriage and then using an actuator to place the stent on the catheter.

16. A method for crimping a stent to a balloon to a balloon catheter, the balloon having balloon markers identifying a proper alignment of the stent with the balloon, comprising:

preparing the balloon catheter for crimping including placing the catheter on a movable carriage, then moving one of the catheter and the stent relative to the other using an actuator-controlled mechanism to position the stent on the catheter;

verifying that the stent is aligned with the balloon including collecting at least one image of the stent and balloon and then analyzing the image to verify that the stent is between the balloon markers;

after the verifying step, inserting the stent and balloon into a crimper; and crimping the stent to the balloon, including a first crimping of the stent to reduce the stent diameter to a first diameter, repeating the verifying step after the first crimping, and after the verifying step, a second crimping to reduce the stent diameter to a second diameter, wherein the second diameter is less than the first diameter.

17. The method of claim 14, wherein the polymer stent is PLLA and the diameter of the stent before crimping is about 2.5 times larger than the final crimp diameter.

18. The method of claim 16, wherein prior to activating the actuator-controlled mechanism, the stent is placed on the catheter such that it is biased towards the catheter proximal end.

19. The method of claim 16, wherein the stent is a polymer stent, further including the step of reducing a static charge including applying an antistatic spray to the crimper head and stent before crimping.

20. The method of claim 13, wherein after the first crimping step the stent is capable of being longitudinally shifted on the balloon and after the second crimping step the stent is not capable of being longitudinally shifted on the balloon.

21. The method of claim 13, wherein the stent diameter is reduced to a first diameter after the first crimping step and a second diameter after the second crimping step, the second diameter being less than the first diameter.

* * * * *